United States Patent [19]

Masson et al.

[11] Patent Number: 5,607,666
[45] Date of Patent: Mar. 4, 1997

[54] COSMETIC OR DERMATOLOGICAL POWDER, ITS PREPARATION PROCESS AND ITS USES

[75] Inventors: Gerard Masson, Cully, Switzerland; Didier Candau, Bievres; Carine Khayat, La Varenne, both of France

[73] Assignee: L'Oreal, Paris, France

[21] Appl. No.: 361,373

[22] Filed: Dec. 22, 1994

[30] Foreign Application Priority Data

Dec. 22, 1993 [EP] European Pat. Off. .............. 93121169

[51] Int. Cl.⁶ .............................. A61K 7/00; A61K 31/74
[52] U.S. Cl. .......................... 424/69; 424/401; 424/78.03; 514/938
[58] Field of Search .................... 424/69, 78.03, 424/401; 514/938

[56] References Cited

U.S. PATENT DOCUMENTS

| | | | |
|---|---|---|---|
| 3,800,034 | 3/1974 | Kircher | 424/63 |
| 4,988,503 | 1/1991 | Macchio | 424/63 |
| 5,034,216 | 7/1991 | Barone | 424/63 |
| 5,338,535 | 8/1994 | Berndt | 424/69 |
| 5,362,482 | 11/1994 | Yoneyama | 424/69 |

*Primary Examiner*—Sallie M. Gardner
*Attorney, Agent, or Firm*—Oblon, Spivak, McClelland, Maier & Neustadt, P.C.

[57] ABSTRACT

Powders that have been obtained from a homogenized and dehydrated oil-in-water emulsion containing (a) a structuring and emulsifying agent, (b) at least one fat, (c) at least one cosmetically active substance, and (d) an aqueous phase, may be reconstituted to regive the oil-in-water emulsion by hydration. The powder can be used, as is, in cosmetic or dermatological products.

8 Claims, No Drawings

COSMETIC OR DERMATOLOGICAL POWDER, ITS PREPARATION PROCESS AND ITS USES

BACKGROUND OF THE INVENTION

1. Field of the Invention

The present invention relates to cosmetic and/or dermatological powders, and to a process for preparing such powders. Such powders can be used to obtain ingestible capsules. The present invention especially relates to a dehydrated oil-in-water emulsion (O/W), that can be used as is and that can be reconstituted.

2. Discussion of the Background

The anhydrous products that are commonly used in cosmetology are oily (water-in-oil) and have an oily touch. These products are rather well adapted for an application on dry skin.

Unfortunately, such products are not easy or nice to handle, because they are often fluid or liquid. On the other hand, such products are not satisfactory for hydrating normal to oily skin, do not penetrate well in the skin, and leave an oily and shiny film on the skin.

Thus, there remains a need for anhydrous cosmetic and/or dermatological powders that can be reconstituted, can contain at least one fatty element without suffering from the disadvantage of "heaviness" when applied to the skin. There also remains a need for a method of preparing such powders.

SUMMARY OF THE INVENTION

Accordingly, it is one object of the present invention to provide anhydrous cosmetic and/or dermatological powders that may be reconstituted.

It is another object of the present invention to provide anhydrous cosmetic and/or dermatological powders that can contain at least one fatty element without encountering disadvantages such as the "heaviness" once on the skin, of the previous anhydrous products.

These and other objects of the present invention, which will become apparent during the following detailed description, have been achieved by the inventors' discovery that cosmetic and/or dermatological powders, with a base of an homogenized and dehydrated oil-in-water emulsion, said emulsion comprising (a) a structuring and emulsifying agent, (b) at least one fatty element, (c) at least one cosmetically and/or dermatologically active substance, and (d) an aqueous phase, are able to be reconstituted to said oil-in-water emulsion by hydration.

DETAILED DESCRIPTION OF THE PREFERRED EMBODIMENTS

In the context of the present application, the term "oil-in-water emulsion" includes all types of dispersions of oil in water.

The powder, according to the present invention, offers the benefits of being applicable on oily or normal skins, of being easy and quick to use, of easy dosage, of keeping the hydrating capabilities of fatty elements, and of not needing an obligatory liquid additive like water; it can be used as is.

Cosmetic products in such a form allow the incorporation of compounds that have different physical-chemical characteristics.

In fact, such powders can simultaneously contain fatty elements and detergents. This allows for instance, the cleansing of the skin while being hydrated and reconstituted. Thus, the present compositions represent a new concept in cosmetic or dermatological products with varied applications, and not intended for a specific type of skin.

Furthermore, these powders are storage stable, lasting for a long time in an aqueous medium (i.e. vitamins), and thus their activity does not become diminished. In the past, these products were isolated from water (i.e. in separate containers).

According to the present invention, the powder also offers the advantage of having a low volume after crushing, which makes its handling easier.

According to the present invention, the powder can eventually be mixed with a liquid with a water base. By water-based, we mean a liquid that has been selected among water, milk, vegetable or fruit juices, and herb teas. Generally, the preparation of this emulsion, therefore of its aqueous phase, and its hydration are made with water.

The dehydrated emulsion must have been especially treated, so that the fatty element and the cosmetically active substance are encapsulated in a matrix. By encapsulated, it is meant that all liquid or solid matter is retained in its entirety, or thinly dispersed in a solid structure that acts as a frame, a support or an envelope for protection or conservation.

The powder, according to the invention can have a residual moisture content of around 2 and 4% by weight, based on the total weight of the powder.

According to the present invention, the powder contains an active cosmetic substance. It can be either the lipid phase as such, like essential oils, or literally a cosmetic agent, or a combination of both. The powder of this invention may contain between 1 an 94% by weight, and preferably between 10 and 70% by weight, based on the total weight of the powder of fatty elements and of cosmetically active substances.

The fatty element to be used can be selected from mineral oils like paraffin or petroleum oils, silicone oils, vegetable oils like coconut, almond, apricot, corn, jojoba, olive, avocado, sesame, palm, eucalyptus, rosemary, lavender, pine, thyme, mint, cardamon, orange blossoms, soy beans, bran, rice, colza, and castor oils, animal oils and fats like tallow, lanolin, butter oil, fatty acid esters, fatty alcohol esters, waxes whose fusion point is the same as the skin's (animal waxes like bee's wax, carnauba or candellila waxes, mineral waxes like micro-crystalline waxes and synthetic waxes like polyethylene or silicone waxes). All acceptable oils used in cosmetology can be used, like the ones that have been mentioned in the CTFA's book, Cosmetic Ingredient Handbook, First edition, 1988, The Cosmetic, Toiletry and Fragrance Association, Inc., Washington.

The term cosmetically or dermatologically active substance means active cosmetics chosen from anti-acne agents, anti-microbial agents, anti-perspiration agents, astringents, deodorants, hair removers, external analgesics, agents for hair conditioning, skin conditioning, sun protection, vitamins, catechines, flavonoids, ceramides, fatty substances, polyunsaturated fatty acids, essential fatty acids, keratolytic agents, enzymes, anti-enzymes, moisteners, anti-inflammatory substances, detergents, perfumes, and mineral substances for synthetic coverings. These substances represent from 1 to 20% by weight, based on the total weight of the powder.

The detergent or foaming agents are the disodic cocoamphodiacetate salt (MIRANOL C2M of RHONE POU- LENC); the lauroylether sulfosuccinate disodic salt (SETACIN 103 of ZSCHIMMER); the vegetable protein acylates (PROTEOL VS22 of SEPPIC); the cocoyl glutamate triethanolamine salt (acylglutamate CT12 d'AJINOMOTO); the lauroyl sarcosinate sodium salt (ORAMIX 130 of SEPPIC); the glucoside decyl-ether (ORAMIX NS10 of SEPPIC); the sodium sulfate lauroyl ether (NEOPON LOS RO of WITCO).

Pasty active compounds like lanolin by-products (acetyl lanolin), lanolin, and lanolin alcohols; cholesterol by-products, like cholesterol esters (12 cholesteryl hydroxy stearate); pentaerythritol hydroxylated esters (SALACOS 168M), linear mono-esters like butyl stearate, arachidyl propionate or stearyl heptanoate, and triglycerides with a fatty chain less than $C_{16}$ can also be used.

These substances are either water-soluble, lipid-soluble, or lipid-soluble and water-soluble at the same time, or dispersible. They can be chosen from the compounds that are in CTFA at pages 51 to 101.

The structuring and emulsifying agent that is present in the powder according to the present invention can be present in a quantity that can be from 4 to 30% by weight, and preferably from 4 to 15% by weight, based on the total weight of the powder.

These compounds which at one time possess the two properties can be chosen from among the hydro-colloids and the biopolymers. By hydro-colloids, it is meant polysaccharides which can be modified especially by a less hydrophobic chain.

By biopolymers, it is meant proteins of animal or vegetable origin and their by-products, or hydrolysates, like sodium caseinate, and wheat and soy protein.

The powder can contain a surface wetting agent that would increase the wettability of the powder when the reconstitution of the emulsion takes place. This agent is generally present in an amount from 0 to 30% by weight, and preferably from 1 to 20% by weight, based on the total weight of the powder. This surface agent especially allows the increase of the speed of rehydration of the powder using the dispersion or emulsion.

This surface agent can be chosen from the hydrophillic surface agents, like glycols, such as hexylene glycol, butylene-1,2 glycol, ethyl-2-hexyl sulfosuccinate; oxyethylene octylphenol (9), and the salts derived from cocoyl and lauroyl collagen, sorbitan palmitate, and the polyoxyethylene byproducts of sorbitol palmitate esters, salts of fatty chain quaternary ammonium.

According to the present invention, the powder can contain other excipients such as colorants, abrasives, opacifiants and complexants.

In another embodiment, the present invention provides a process for preparing the powder as described. The present process comprises making an oil-in-water emulsion, in homogenizing this emulsion, and in dehydrating said emulsion to make said powder.

According to the way this process is performed, the emulsion that is used is such that it has a dry matter content that is between 5 and 70% by weight, and preferably between 10 and 60% by weight, based on the total weight of the emulsion. Such an amount of dry matter permits obtaining an emulsion with a viscosity such that it is sufficiently fluid to be pumped.

The content of dry matter gives, in the emulsion, a content of fat or of a cosmetically or dermatologically active substance between 0.1 and 51% by weight, and a content of structuring and emulsifying agent between 0.1 and 18% by weight, based on the total weight of the emulsion.

The aqueous phase can be prepared at conventional temperatures (e.g., 0° to 85° C.) providing that the structuring and emulsifying agent is soluble at the temperature being used. It is possible to work at a temperature between 40° and 80° C., in order to obtain a quicker dissolution of certain ingredients.

It is possible as well to prepare the mixture at a lower temperature, around 4° to 10° C., in order to maintain good conditions with regard to bacterial contamination.

In a similar manner, one can prepare a fat phase at the same temperature as the aqueous phase, and they are added such that, in the resulting emulsion, the content of fat is between 10 and 60% by weight, based on the total weight of the emulsion.

The relative amounts of the constituents as defined according to this invention guarantees an emulsion with a good homogeneity and stability, and also allows an excellent reconstitution of the emulsion.

One then makes an emulsion by slowly mixing the fat and aqueous phases, for example by slowly incorporating the fat phase into the aqueous phase and maintaining a constant shaking movement, and, in the absence of a preservative agent, at a temperature around 4° to 10° and 65° to 75° C., again for bacteriological reasons.

One then obtains an oil-in water emulsion, having a pH depending on its composition, generally between 4 and 9.

The percentage of dry matter of said emulsion is preferably between 10 and 60 by weight, based on the total weight of the composition, in order to allow the pumping, the homogenization and the rehydration (or drying).

One then homogenizes the emulsion, under high pressure, in order to reduce the average size of the droplets of the fatty phase down to about 1 μm, or less. It has been observed that the homogenization improves the qualities of rehydration of the rehydrated powder, as well as its functional characteristics, such as, for instance, the ability to form a firm and stable gel, which is important when a product having the appearance, texture and consistency of a cosmetic product with classic features is desired.

A two stage homogenizer can be used, according to standard methods. However, one should be careful not to use too high a pressure, around 350 bars ($35 \times 10^6$ Pa), in order to avoid any denaturation of certain structuring or emulsifying agents which would trigger a loss of functionality and would lead to the irreversible separation of the phases of the emulsion. The homogenization can be performed at a temperature between 4° and 45° C., for bacteriological reasons. The homogenized emulsion is then dehydrated by any known procedure, like lyophilization or atomization, or any other drying process in a vacuum. One obtains a powder that eventually can be compressed by any known method. The temperature of the hot air that is used for the drying process is around 100° to 160° C. and the temperature for removing the powder is between 30° and 90° C.

The powder that is obtained can also be compressed to take up less volume and to make it easier for packaging, preservation, storage and use. Before eventually compressing the powder, it can be submitted to an additional granulating stage to homogenize the granulometry of the powder.

One then obtains a powder that is ready for use, as is or right after reconstituting the emulsion by adding liquid.

The later use of the powder depends on the active substances and eventually on the quantity of liquid that is added to reconstitute the emulsion, and therefore, on its viscosity that determines its consistency, more firm for a cream for treatment or a moisturizing cream, and more or less liquid for a cleansing cream, a facial oil, or shampoo.

In general terms, by adding liquid in a weight ratio of powder/liquid equal to 10:1 to 1:1, one can reconstitute a product that would have the consistency of a classic cosmetic or dermatological product.

According to the present invention the powder also offers the advantage of being immediately rehydratable in the cold, in a liquid such as water, and allows the reconstitution of an homogeneous and stable emulsion, without separation of the phases. Furthermore, the powder that is obtained is very stable and can be kept for 2 to 8 weeks at room temperature without any noticeable phase separation or any other damage (i.e. microbiological). It is possible to add, after reconstitution, other cosmetic or dermatological ingredients.

The present powder may be used as previously defined for cosmetic or dermatological emulsions or in ingestible capsules.

Other features of the invention will become apparent in the course of the following descriptions of exemplary embodiments which are given for illustration of the invention and are not intended to be limiting thereof.

EXAMPLES

Example 1

A mixture containing 60 g of sodium caseinate, 30 g of xanthan gum and 695 g of water is mixed for 30 minutes at room temperature. To this aqueous phase 215 g of apricot oil that has been cooled to 10° C. is added, while shaking constantly in order to obtain an oil-in-water emulsion, having a pH around 7.

A perfume and a colorant like β-carotene are added, and the emulsion is homogenized and dehydrated by evaporation. The emulsion is eventually reconstituted by adding one part by weight of water to one part by weight of powder. A base of cream for treatment is obtained. By preparing the base in this way it remains stable, without degradation of the active ingredient, for a minimum of 8 hours.

Example 2

One proceeds as in Example 1 with the same aqueous phase, but one adds to this phase 210 g of apricot oil and 5 g of vitamin E. One homogenizes the emulsion and one dehydrates it as was done previously. One obtains a dry emulsion that one rehydrates at the rate of 2 parts by weight of powder for one part by weight of water in order to obtain a protective cream.

Example 3

One prepares an aqueous phase containing 60 g of sodium caseinate, 5 g of carboxy methyl cellulose, 5 g of guar rubber, 700 g of water and 15 g of glycerin which one mixes for 30 minutes at ambient temperature. One adds to this aqueous phase a lipid phase containing 100 g of apricot oil, 50 g of silicon oil and 65 g of paraffin oil, maintaining constant stirring in order to obtain an oil-in-water emulsion, having a pH on the order of 7.

One homogenizes the mixture as in Example 1 in order to obtain an emulsion having a percentage of dry material of 28.5% by weight based on the total weight of the emulsion. One dehydrates the emulsion by lyophilization. One reconstitutes the product by the addition of one part by weight of water per part by weight of powder, and one obtains a perfectly stable nutritive cream.

Example 4

One prepares an aqueous phase containing 60 g of sodium caseinate, 50 g of corn starch and 590 g of water. One mixes this aqueous phase with 300 g of apricot oil which one homogenizes as in Example 1.

One dehydrates the mixture by means of pulverization drying and one obtains a powder containing 2.5% by weight of residual moisture. One reconstitutes the emulsion by the addition of one part by weight of powder for 0.5 parts by weight of water, and one obtains a mask for the face. One can add to the reconstituted emulsion any dermatological or cosmetic active ingredient in accordance with prior art.

Example 5

One prepares the emulsion of Example 2 in which the fatty phase contains 175 g of apricot oil, 5 g of vitamin E, 10 g of vitamin C, and 15 g of beta-kerotene which one dehydrates by spraying at an input temperature greater than 100° C. and lower than 120° C. The resulting powder is encapsulated in soft capsules of ingestible gelatin, serving as vitamin food supplements.

Example 6

| | |
|---|---|
| Triglyceride of vitamin F | 4.4% |
| Preservative | 0.5% |
| Sodium caseinate | 5.4% |
| Water qsp | 100% |
| Xanthan gum and casein | 3.1% |
| Copper glucanate | 0.0005% |
| Tyrosine | 0.02% |
| Phenylalanine | 0.008% |
| Tocopherol | 0.002% |
| Niacinamide | 0.002% |
| Ascorbic acid | 0.06% |
| β-carotene | 0.002% |

After formation of the O/W emulsion in the traditional manner the latter is homogenized and dried by spraying; the resulting powder can be put in the form of tablets by any conventional means.

The resulting powder can also be encapsulated in a soft gelatin capsule.

The two forms of the composition are used as vitamin supplements for oral cosmetics.

Example 7

| | |
|---|---|
| Mineral oil | 8% |
| Preservative | 0.5% |
| Sodium caseinate | 5.4% |
| Water qsp | 100.00% |
| Xanthan gum and casein | 3.1% |
| Lauryl ether sulfate of sodium with 2.2 moles of ethylene oxide | 5.0% |
| Polyglycerated dodecanediol with 3.5 moles of glycerol | 6.3% |
| Ethylenediaminetetracetate | 0.1% |
| Reticulated quaternary hydroxyethyl cellulose | 0.2% |

Following homogenization the O/W emulsion is dried by spraying; the resulting powder has a good detergent capability, and can be used in dry shampooing to clean the hair and scalp.

Example 8

| | |
|---|---|
| Mineral oil | 4.50% |
| Preservative | 0.5% |
| Sodium caseinate | 5.4% |
| Water qsp | 100.00% |
| Xanthan gum and casein | 3.1% |
| Sodium lauryl ethoxy sulfate | 8.9% |

Following homogenization the O/W emulsion is dried by spraying. The resulting powder is quite powdery and not fatty, and it allows one to obtain a cleaning powder which is foamy and rinsable in water.

Example 9

| | |
|---|---|
| A mixture consisting of sunflower oil, sunflower hybrid, and musk rose, black currant pips (31/60/5,95/3) | 5% |
| Liquid fraction of karite nut butter | 3.4% |
| Glyceride esters of essential fatty acids (linoleic/oleic/linolenic) | 3.5% |
| Preservatives | 0.6% |
| Xanthan gum | 0.2% |
| Isohexadecane | 3.5% |
| Water qsp | 100% |
| Hydrolyzed soy protein | 7.9% |

Following homogenization, O/W emulsion is dried by spraying, the resulting powder is white, is soft to the touch and has a pleasant non-greasy feel.

When it is applied, this powder slowly releases the oil that it contains allowing one to protect and nourish the skin. This powder can be used as a health care powder.

Example 10

| | |
|---|---|
| Karite nut butter | 1.5% |
| Cetearyl octanoate and isopropyl myristate | 5% |
| Preservatives | 0.6% |
| Xanthan gum | 0.2% |
| Dimethicone | 3.5% |
| Water qsp | 100% |
| Ascorbic acid | 5% |
| Hydrolyzed soy protein | 2.8% |

Following homogenization of the emulsion, one dries the emulsion by spraying, and one obtains a non-greasy and non-sticky white powder which allows one to achieve good stability of vitamin C during storage.

The resulting powder can be used as is or reconstituted in order to obtain a product which is efficacious for firming the skin, and for removing pigmentation of pigmented spots caused by the sun or aging.

Example 11

| | |
|---|---|
| Apricot oil | 1% |
| Shorea butter | 5% |
| Cetearyl octanoate and isopropyl myristate | 5% |
| Vitamin A | 0.5% |
| Preservatives | 0.6% |
| Xanthan gum | 0.2% |
| Dimethicone | 3.5% |
| Water qsp | 100% |
| Soy protein and xanthan gum | 3.5% |
| Hydrolyzed soy protein | 3.6% |

Following homogenization, the emulsion is dried by spraying, one obtains a white powder which is not sticky and not greasy when touching the product, and which allows one to achieve good stability of vitamin A during storage of the product.

The powder can be used as is, unreconstituted in order to obtain a product which is efficacious against signs of aging.

This application is based on European Patent Application 93-121169.2 filed on Dec. 22, 1993, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A cosmetic or dermatological powder obtained from an oil-in-water emulsion which is homogenized and dehydrated, said emulsion comprising: (a) a hydrocolloidal agent and a biopolymer as structural and emulsifying agents, (b) at least one fatty substance, (c) at least one substance which is cosmetically or dermatologically active, and (d) an aqueous phase, said powder having a residual water content between 2 and 4% by weight, based on the total weight of said powder, said powder further being capable of being reconstituted by the step consisting essentially of rehydration to obtain an oil-in-water emulsion, wherein the hydrocolloidal agent is selected from the group consisting of xantham gum, carboxy methyl cellulose, and corn starch, and the biopolymer is selected from the group consisting of sodium caseinate, casein, soy protein, and hydrolyzed soy protein.

2. The powder of claim 1, wherein said fatty substance (b) is present in an amount between 1 and 94% by weight, based on the total weight of said powder.

3. The powder of claim 2, wherein said fatty substance (b is present in an amount between 10 and 70% by weight, based on the total weight of said powder.

4. The powder of claim 1, wherein said structural and emulsifying agent (a) is present in an amount between 4 and 30% by weight, based on the total weight of said powder.

5. The powder of claim 4, wherein said structural and emulsifying agent (a) is present in an amount between 4 and 15% by weight, based on the total weight of said powder.

6. The powder of claim 1, wherein said fatty substance is selected from the group consisting of the oils of cocoa, apricot, sweet almonds, corn, jojoba, olive, avocado, tallow, sesame or palm, paraffin, vaseline, silicon, waxes, esters of fatty acids, and esters of fatty alcohols.

7. The powder of claim 1, wherein said cosmetically or dermatologically active substance (c) is selected from the group consisting of anti-acne agents, anti-microbial agents, anti-perspiration agents, astringents, deodorants, hair removers, external analgesics, agents for hair conditioning, skin conditioning, sun protection, vitamins, catechines, flavonoids, ceramides, fatty substances, polyunsaturated fatty acids, essential fatty acids, keratolytic agents, enzymes, anti-enzymes, moisteners, anti-inflammatory substances, detergents, perfumes, and minerals.

8. The powder of claim 1, further comprising from 0 to 30% by weight, based on the total weight of said powder, of a surface wetting agent.

* * * * *

UNITED STATES PATENT AND TRADEMARK OFFICE
CERTIFICATE OF CORRECTION

PATENT NO. : 5,607,666
DATED : MARCH 4, 1997
INVENTOR(S) : GERARD MASSON ET AL

It is certified that error appears in the above-identified patent and that said Letters Patent is hereby corrected as shown below:

Column 2, line 34, "1 an 94%" should read --1 and 94%--.

Column 4, line 28, "oil-in water" should read --oil-in-water--.

Column 8, line 32, "xantham" should read --xanthan--;
        line 62, "minerals" should read --mineral substances for synthetic covering--.

Signed and Sealed this

Fourth Day of August, 1998

Attest:

BRUCE LEHMAN

Attesting Officer        Commissioner of Patents and Trademarks